US011922416B2

(12) United States Patent
Anderson et al.

(10) Patent No.: US 11,922,416 B2
(45) Date of Patent: *Mar. 5, 2024

(54) ATOMTRONICS AS A SERVICE

(71) Applicant: ColdQuanta, Inc., Boulder, CO (US)

(72) Inventors: Dana Zachary Anderson, Boulder, CO (US); Seth Charles Caliga, Lafayette, CO (US); Farhad Majdeteimouri, Broomfield, CO (US)

(73) Assignee: ColdQuanta, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/722,352

(22) Filed: Apr. 17, 2022

(65) Prior Publication Data
US 2022/0237613 A1    Jul. 28, 2022

Related U.S. Application Data

(63) Continuation-in-part of application No. 16/914,496, filed on Jun. 29, 2020, now Pat. No. 11,334,812.
(Continued)

(51) Int. Cl.
*G06Q 20/10*         (2012.01)
*G06Q 20/40*         (2012.01)
*G16C 10/00*         (2019.01)

(52) U.S. Cl.
CPC ........... *G06Q 20/401* (2013.01); *G16C 10/00* (2019.02)

(58) Field of Classification Search
CPC ........... G06N 10/00; B82Y 10/00; G06F 1/31; G21K 1/00; H04L 67/146; H04L 67/306
(Continued)

(56) References Cited

U.S. PATENT DOCUMENTS 10,504,033 B1    12/2019  King
11,334,812 B2 *  5/2022   Anderson ............. H04L 67/306
(Continued)

OTHER PUBLICATIONS

Caliga, Seth C., "Experimental realization of atomtronic circuit elements in non-equilibrium ultracold atomic systems", Ph.D. Thesis, University of Colorado, 2016, pp. 1-153, Boulder, CO.
(Continued)

*Primary Examiner* — Nicole M Ippolito
(74) *Attorney, Agent, or Firm* — Van Pelt, Yi & James LLP; Clifton Leon Anderson

(57) ABSTRACT

An atomtronics station and a cloud-based server cooperate to provide Bose-Einstein condensates as a service (ATaaS). The atomtronics station serves as a system for implementing "recipes" for producing, manipulating, and/or using atomtronic devices based on cold atoms that are, in some respects, analogous to classical electronic devices based on electricity. The cloud-based server acts as an interface between the station (or stations) and authorized users of account holders. To this end the server hosts an account manager and a session manager. The account manager manages accounts and associated account-based and user-specific permissions that define what actions any given authorized user for an account may perform with respect to an atomtronics station. The session manager controls (in some cases, real-time) interactions between a user and an atomtronics station, some interactions allowing a user to select a recipe based on results returned earlier in the same session.

20 Claims, 7 Drawing Sheets

Related U.S. Application Data

(60) Provisional application No. 62/990,537, filed on Mar. 17, 2020.

(58) Field of Classification Search
USPC .......................................................... 250/251
See application file for complete search history.

(56) References Cited

U.S. PATENT DOCUMENTS

| | | |
|---|---|---|
| 2017/0223094 A1 | 8/2017 | Johnson |
| 2017/0372427 A1 | 12/2017 | Johnson |
| 2019/0164076 A1 | 5/2019 | Kim |
| 2021/0049494 A1 | 2/2021 | King |
| 2021/0410266 A1 | 12/2021 | Saffman |
| 2023/0110628 A1 | 4/2023 | Paul |

OTHER PUBLICATIONS

Castelvecchi, Davide, "IBM's quantum cloud computer goes commercial", Nature 543, 159, Mar. 9, 2017, https://www.nature.com/news/ibm-s-quantum-cloud-computer-goes-commercial-1.21585.

Devitt, Simon J., "Performing Quantum Computing Experiments in the Cloud", Physical Review A. 94. 10.1103/PhysRevA.94.032329.

IBM, "IBM Quantum Experience is quantum on the cloud", web page downloaded Sep. 20, 2020, https://www.ibm.com/quantum-computing/technology/experience/?p1=Search&p4=43700050385922780&p5=e&cm_mmc=Search_Google-_-1S_1S-_-WW_NA-_-ibm%20quantum%20experience_e&m_mmca7=71700000061253574&cm_mmca8=aud-384354108630%3Akwd-397733481108&cm_mmca9=CjwKCAjw-5v7BRAmEiwAJ3DpuLwvDGM8dXqhr8sdgKddDlc2Nb4aPqWi2BinQ/.

IBM, Quantum Starts Here, Sep. 20, 2020.

Linke, N. M., "Experimental Comparison of Two Quantum Computing Architectures", Proceedings of the National Academy of Sciences Mar. 2017, 114 (13) 3305-3310; DOI: 10.1073/pnas.1618020114.

Protalinski, Emil, "D-Wave announces Leap 2, its cloud service for quantum computing applications", VentureBeat, Feb. 26, 2020 downloaded from website on Sep. 20, 2020, https://venturebeat.com/2020/02/26/d-wave-announces-leap-2-its-cloud-service-for-quantum-computing-applications/.

Wikipedia, "IBM Q Experience", Wikipedia article downloaded Sep. 20, 2020, https://en.wikipedia.org/wiki/IBM_Q_Experience.

Inardo, Brad A.; "Single Atom Delivery into a Bottle Beam Trap Using an Optical Conveyor Belt and an Ultracold Gain Mechanism in a Matterwave Transistor Oscillator" A Thesis submitted to the Faculty of the Graduate School of the University of Colorado in partial fulfillment of the Requirements for the Degree of Doctor of Philosophy, Department of Physics, Boulder, Colorado, 2018.

\* cited by examiner

ATOMTRONICS AS A SERVICE

BACKGROUND

Atomtronics is an emerging sub-field of ultracold atomic physics that encompasses a broad range of topics featuring guided atomic matter waves. The systems typically include components analogous to those found in electronic and optical systems, such as beam splitters and transistors. For example, atomtronic transistors have been developed that include source, gate, and drain structures analogous to a field-effect transistor. Such transistors have been shown to realize a gain mechanism such that the atom flux through the gate-drain barrier exceeds the atom flux through the source-drain barrier. Furthermore, the atom flux through the gate-drain barrier has been shown to be in the form of Maxwell matter waves, the matter wave analog of laser beams.

Ultracold atomic physics typically involves the formation of Bose-Einstein condensates by cooling atoms confined to ultra-high vacuums (UHV) below $10^{-9}$ Torr to ultracold temperatures (e.g., 50 nanoKelvin). The required equipment is expensive, requires a high degree of expertise to operate, and is typically only found in research labs. In practice, development of atomtronics is limited to ultracold atom physicists and their graduate students. What is needed is access to atomtronics by a more diverse population and without the major investment required to purchase, install, and maintain the necessary equipment.

DETAILED DESCRIPTION

The present invention provides for atomtronics as a service (ATaaS) such that account holders can access an atomtronics system remotely over the Internet or other network. The present invention further provides for real-time, exclusive, interactive production and/or manipulation of atomtronic components. ATaaS allows account holders access to atomtronics without the burden of purchasing and maintaining the associated equipment. Furthermore, potential purchasers of the equipment are provided a way to evaluate the equipment prior to purchase. Thus, ATaaS allows more people to study and to develop atomtronics devices and applications.

Figure 1:
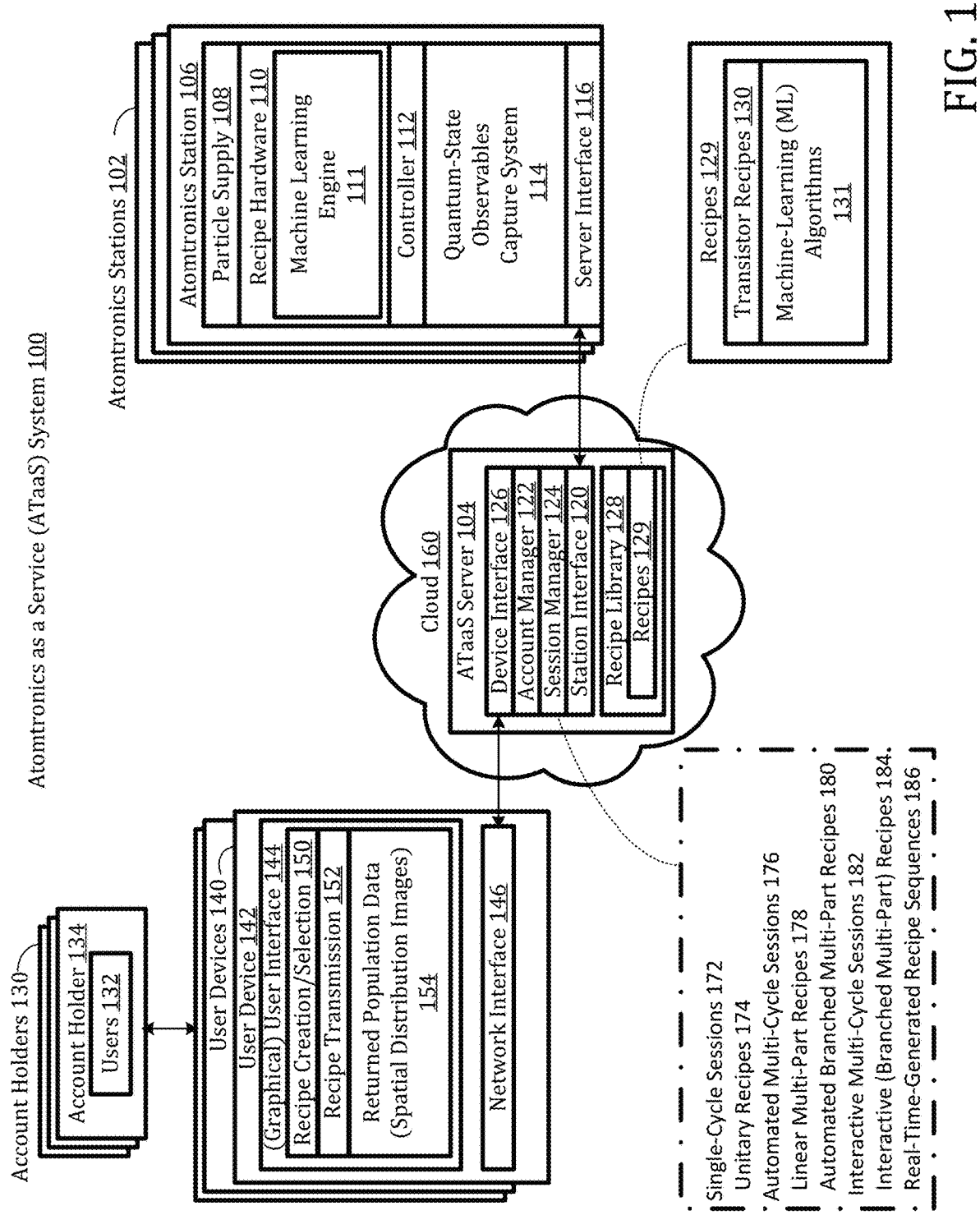
FIG. 1 is a schematic illustration of an atomtronics as a service (ATaaS) system.

As shown in FIG. 1, an ATaaS system 100 includes a set 102 of atomtronic stations and a cloud-based ATaaS server 104. Set 102 includes one or more atomtronic stations including representative atomtronic-station 106. Atomtronic station 106 includes a particle supply 108, recipe hardware 110 including a machine-learning engine 111, a controller 112, a quantum-state capture system 114, and a server interface 116.

Particle supply 108 can, for example, supply rubidium 87 ($^{87}$Rb) atoms, which can assume different quantum states corresponding to energy levels of its single-electron outer shell. When cooled to a sufficiently low temperature, as determined by a phase-space density, a cloud of $^{87}$Rb atoms can form a Bose-Einstein condensate in which the atoms share a common quantum state. Depending on the embodiment, a particle supply can provide exactly one type of quantum-state carrier or plural types of quantum state carriers (e.g., potassium and cesium).

Recipe hardware 110 is used to process supplied quantum particles according to a recipe. The processing can include cooling, transport, and inducing phase and/or state transitions. The hardware for atomtronics station 106 can include a vacuum system, a laser system, optical path elements, a magnetics system, and an electronics system. In addition, recipe hardware 110 includes a machine-learning engine for use in developing new atomtronics recipes and other recipes calling for optimizations. The components of these systems can overlap; for example, an atom chip can serve as part of a vacuum boundary, conduct currents to form magnetic fields, and include a window for optical access to the vacuum interior. In other embodiments, e.g., involving an all-optical BEC, there is no atom chip. A controller 112, which may be integrated into the electronics system, coordinates the hardware actions to implement a recipe received over server interface 116 from ATaaS server 104.

Quantum-state capture system 114 captures observables of quantum particles to yield wavefunction characterizations. In fact, a recipe can specify which observables are to be captured, as well as how the capture is to be effected. For example, a fluorescence or absorption image of atoms may be captured to characterize a wavefunction (or spatial distribution) of the atoms. The captured observables data, either as collected or in modified form, is transmitted back to a user via ATaaS server 104. ATaaS server 104 includes a station interface 120, an account manager 122, a session manager 124, a device interface 126, and a recipe library 128 of recipes 129. Recipes 129 can include transistor recipes 130 and machine-learning algorithms 131 (for when a new atomtronic optimization is required).

Account manager 122 manages accounts of individual users and corporate entities; this includes managing financial transactions with account holders 130, which determine permissions for each account. In addition, account manager 122 serves to identify, authenticate, and manage permissions of authorized users for each account holder, e.g., authorized users 132 of account holder 134.

Account manager 122 can provide for a variety of account types. For example, accounts can provide for on-demand access, scheduled access, and stand-by access. On-demand access provides priority access pending completion of a currently implementing recipe and any on-demand recipes in the queue ahead of the current one. Scheduled access means access at a future time from a choice of times offered by the session manager and subject to change due to conflicts with higher-priority recipes. Stand-by access means that the recipe will be executed when time is available; the user will be notified when results are available. An account holder may grant some of its authorized users, e.g., system administrators, all the permissions associated with the account type, while it may grant others of its authorized users more restricted sets of permissions.

Authorized users can access ATaaS server 104 via respective user devices 140, which include, but are not limited to, computers and mobile devices. User device 142, for example, includes a graphical user interface 144 and a network interface 146. Graphical user interface 144 provides functionality for recipe creation and/or selection 144, and recipe transmission 152.

An authorized user can select recipes either directly from recipe library 128 on ATaaS server 104 or from a local recipe library on a user device 142. The latter library can be updated using entries in cloud recipe library 128 or by storing recipes created on the user device by the user. Recipes in library 128 may be selectively forbidden to users based on the respective account and user permissions; for example, a user may be able to access transistor recipes 130, but not machine-learning algorithms 131 (which could be used to generate new transistor specifications). The recipes can include: unitary recipes 172 that provide for exactly one recipe request in a session, and multi-recipes 174 that provide for a series of requests allowing a user to see the result of a first portion of a recipe before deciding to proceed on a second or subsequent portion of a multi-recipe. A user with sufficient permissions can create a multi-part recipe by combining unitary recipes or combining at least one unitary recipe with at least one multi recipe.

Herein, an "online session" can include a series of user requests (e.g., recipe transmissions) and responses (observables generated by implementing a recipe) during which the user retains continuous real-time access to an atomtronics station. An "offline session" involves implementing a recipe while the user is offline (as when a recipe submitted by the user is implemented on a stand-by basis or on an unattended scheduled basis). Session manager 124 of ATaaS server 104 tags the received recipe with a session identifier so that any results of the recipe can be returned to the correct device and user.

In addition, session manager 124 uses the tag to maintain inter-cycle continuity among plural session cycles, i.e., recipe-result transactions, where such multiple transactions are permitted (e.g., by the permissions associated with the account and the user). ATaaS server 104 forwards tagged recipes from station interface 120 to server interface 116 of BEC-station 106 (or other station). Observables captured during recipe implementation are returned to ATaaS server 104, which forwards the observables to the device that originated the recipe. GUI 144 for the device can display the observables data as appropriate, e.g., as images, graphs, tables, etc.

ATaaS system 100 provides for different session types including single-cycle sessions, automated multi-cycle sessions, and interactive multi-cycle sessions. Single-cycle sessions 172 typically implement unitary recipes 174. Herein, a "recipe" is a document specifying initial conditions and procedures for yielding a result, typically in the form of a quantum wavefunction or a characterization of a quantum wavefunction. For example, a recipe for a Bose-Einstein condensate would specify the equipment and initial state of an atomtronics station as well as the operations required to generate a Bose-Einstein condensate using that atomtronics station. A single-cycle session typically terminates once the result, e.g., an atomtronic gain measurement, is reported to the user.

Multi-cycle sessions permit additional procedures to be performed after a result is reported. In the case of automated multi-cycle sessions, the procedures follow results without user intervention. Automated multi-cycle sessions 176 can implement linear multi-part recipes 178, which provide no choices to be made regarding which procedures are to be implemented regardless of results, and automated branched multi-part recipes 180 for which procedures following results are selected automatically, e.g., by the session manager based on the results. In an automated multi-cycle session, results may be reported to the session manager each cycle; these results may be forwarded to the user or aggregated so that only the aggregate result is forwarded to the user at the end of the session.

Herein, a "branched" recipe is a recipe that includes alternative procedures to be selected based on a condition, which may be a result from a previous part or a procedure of the recipe, a user input, or some other factor (e.g., time). Branched recipes that condition a selection of alternative procedures on a user input after the respective session begins are termed "interactive", whereas recipes that do not accept such input are termed "automated".

Interactive multi-cycle sessions 182 can provide users with real-time, exclusive, and interactive access to an atomtronics station. Interactive branched multi-part recipes 184 permit users to select between/among branches, taking into account results from previous cycles in the session. In the case of such interactive recipes, the user's choices are specified and limited at the outside by the recipe. In the case of real-time generated recipe sequence 186, the user's choices are not limited by the first recipe requested. However, follow-up recipes may be constrained to initial conditions that match the end conditions of a previous cycle, so the user's choices are not unlimited.

Figure 2:
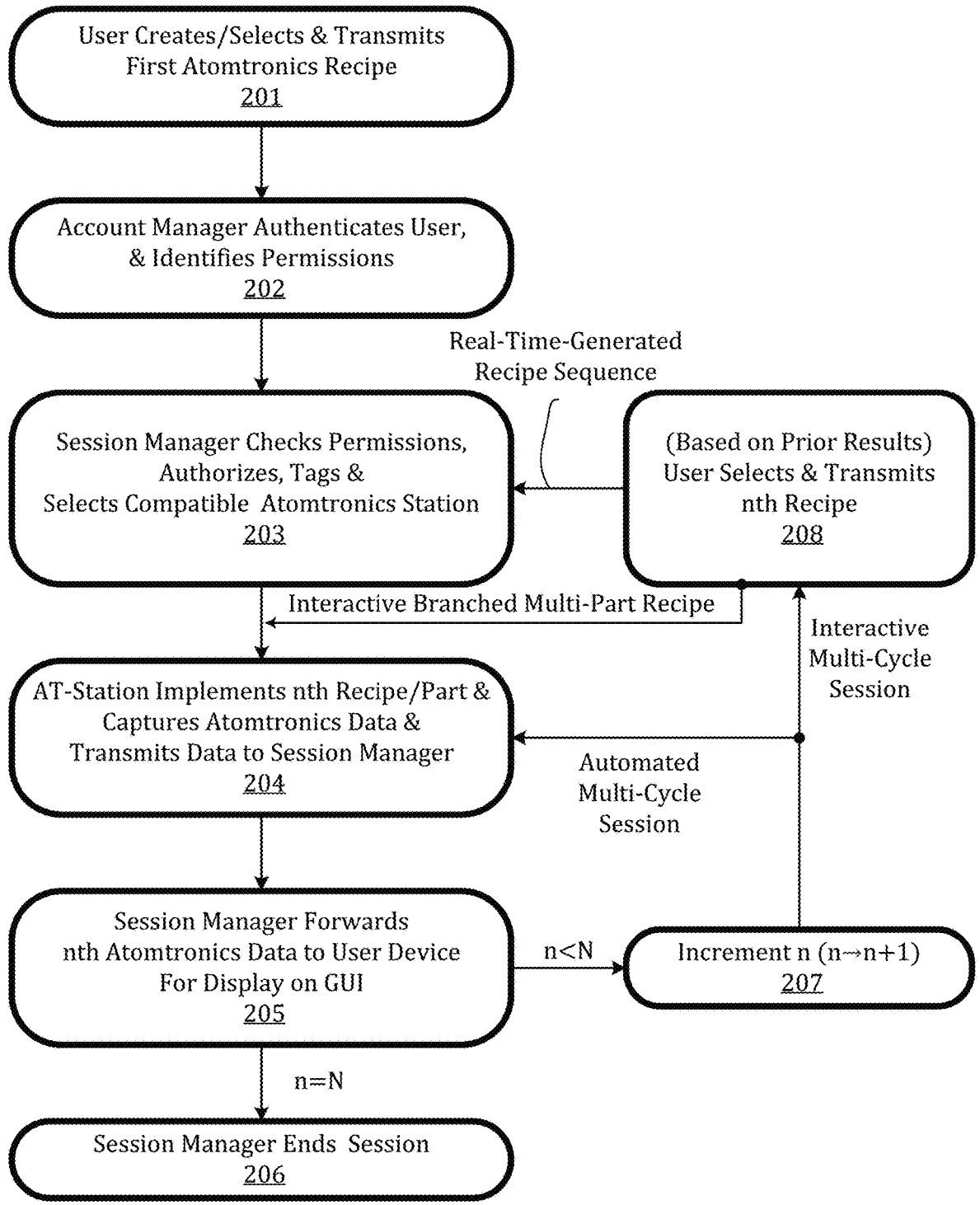
FIG. 2 is a flow chart of an ATaaS process.

An ATaaS- process 200 is flow charted in FIG. 2. At 201, an authorized user creates and/or selects a first atomtronics recipe and transmits it to an ATaaS server. At 202, an account manager running on the ATaaS server authenticates the user and identifies the permissions applicable to that user. These permissions are those associated with the account that have not been excluded for use by the present user or the present user's role in the account holder.

At 203, a session manager running on the ATaaS server checks the applicable permissions, authorizes the recipe (provided it qualifies given the permissions), tags the recipe with a session identifier, and routes the tagged recipe to a compatible atomtronics station. For example, if the recipe calls for the use of $^{87}$Rb atoms, the session manager can route the recipe to an atomtronics-station set up with an $^{87}$Rb source, rather than to, for example, an atomtronics station set up with only a $^{133}$Cs source. More specifically, the selected atomtronics station and its current state are to be compatible with the first recipe; in the illustrated embodiment, the session manager rejects a subsequent recipe that is incompatible with the selected atomtronics station. In an alternative embodiment, a subsequent recipe requested in the same session may be routed to a different atomtronics station compatible with the subsequent recipe.

At 204, the selected atomtronics station then implements a first (n=1) recipe or part of a multi-part recipe, captures first observables atomtronics data, and transmits a station response to the session manager, the station response being based on the observables data. The capturing may be destructive or non-destructive. For example, many imaging techniques impact the quantum state of the quantum-state carriers; however, there are dispersive phase-contrast imaging techniques that are non-destructive. At 205, the session manager then forwards the first observables data to the user for display on the GUI of the user device. More precisely, the session manager transmits a server response based on the station response and, thus, based on the observables data. In some automated multi-cycle sessions implementing multi-part recipes, observables data is not sent to the user each cycle, but rather data collected over multiple cycles is accumulated and sent collectively to the user, e.g., at the end of the session.

Commonly, the sessions are unitary recipe (N=1) sessions, in which case, the session manager ends the session at 206 once the first observables data is sent to the user device. The session may also end due to a time-out or a user request for disconnection. However, certain premium accounts provide for multi-cycle sessions. In such a case, process 200 proceeds from action 205 to a virtual action 207 of incrementing n, that is n→n+1.

How process 200 proceeds from 207 depends on the type of multi-cycle session. In the case of an automated multi-cycle session implementing a linear or automated branched multi-part recipe, the session returns to 204 to implement a next, nth, part of a multi-part recipe, and proceeds from there to 205. In the case of an interactive multi-cycle session, the session proceeds to 208 to select a next, nth, recipe or recipe part, in some cases based on prior results.

In the case of an interactive multi-cycle session that allows a user to generate a recipe sequence in real-time, that is, as the session progresses, the user selects a next, nth, recipe at 208, e.g., based on results from earlier cycles in the session. The newly selected recipe is then, in effect, vetted as the session returns to 203 and proceeds from 203 to 204 and 205, and so on. Typically, but not in all cases, the atomtronics station selected at 203 is the same across cycles of a session.

In the case of an interactive multi-cycle session implementing an interactive branched multi-part recipe, the choices made by a user at 208 can be constrained to pre-approved recipe parts. After the user selects an nth recipe part, the session can proceed from 208 directly to 204, bypassing vetting at 203. The session can then proceed to 205 and so on until completion.

In the event that the data captured at the most recent capture (action 204) is non-destructive, the next recipe or recipe part can use, as a starting point, the state involved in that capture. If the data capture is destructive, the next recipe can use a state prior to the capture state as a starting point. For example, the system can be reinitialized, and the recipe can start with the release of a new population of rubidium atoms or other quantum-state carriers. Alternatively, an earlier recipe may have left a reservoir of (e.g., pre-cooled) molecules, so the next recipe can begin by drawing a new population from the reservoir (instead of returning to the molecule supply).

Consider a user that desires to tune atomtronic transistor-production parameters to achieve a transistor with a target gain before using the atomtronic transistor. Because conditions within an atomtronics station may degrade or otherwise change with intervening time and usages, it may not suffice to rely on tunings developed in previous sessions. A multi-recipe session allows BEC production parameters to be tuned at nearly the same time as the usage and without intervening sessions. Such real-time, exclusive and interactive usage of an atomtronics station thus provides significant advantages over multiple single-recipe sessions. Herein, a multi-cycle session would not be considered "exclusive", if another's user session altered a quantum state achieved during the session.

Figure 3:
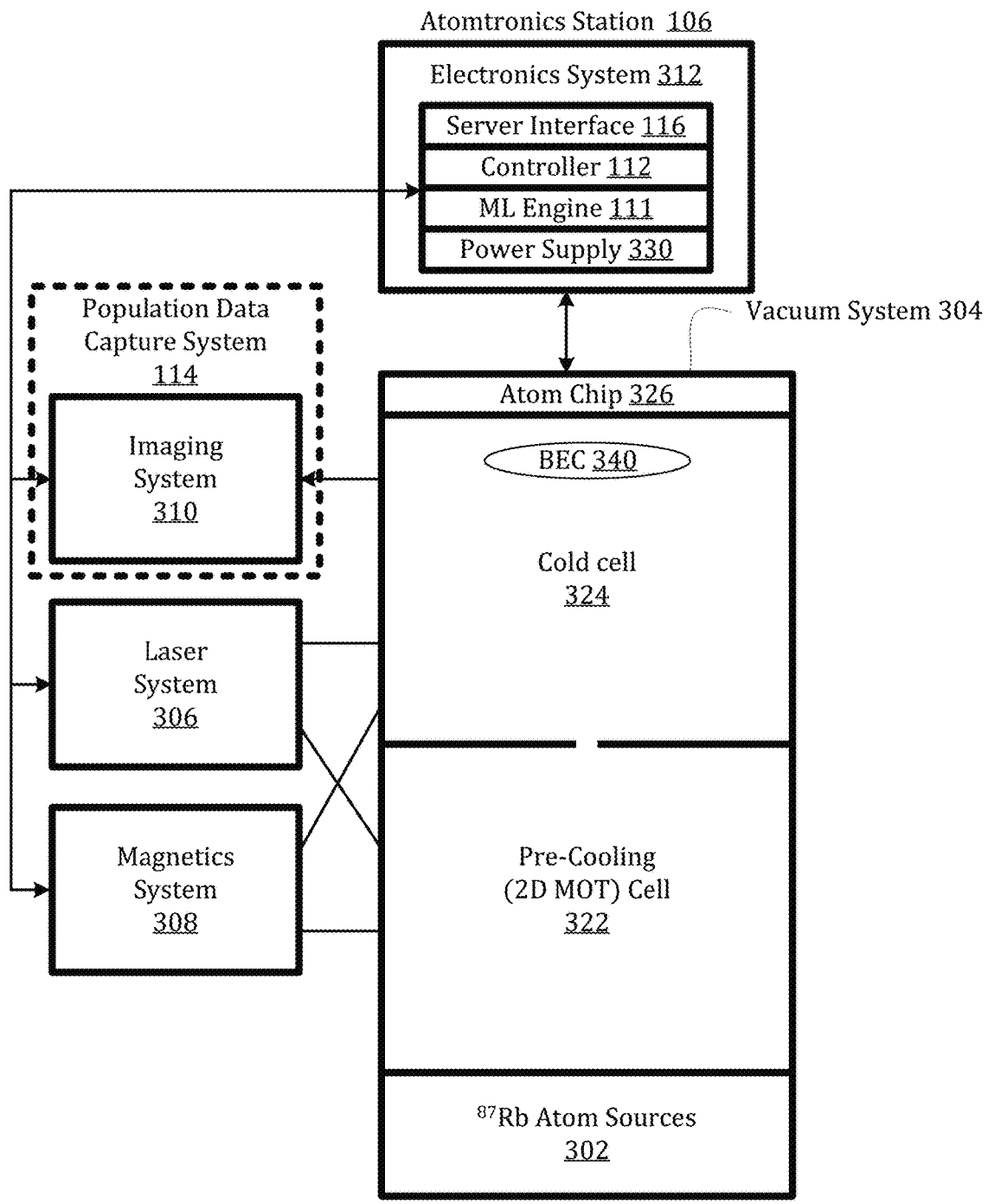
FIG. 3 is a schematic illustration of an atomtronics station of the system of FIG. 1.

Atomtronics-station 106, shown in greater detail in FIG. 3, includes a pair of $^{87}$Rb sources 302, a vacuum system 304, a laser system 306, a magnetics system 308, an imaging system 310, and an electronics system 312. Vacuum system 304 includes a pre-cooling cell 322 and a cold cell 324, which is capped by an atom-chip 326 that forms part of the vacuum boundary for vacuum system 304. Electronics system 312 includes controller 112, server interface 116, and power supply 330. Sources 302 serve as quantum particle supply 108 (FIG. 1). Recipe hardware 110 (FIG. 1) includes vacuum system 304, laser system 306, magnetics system 308, and power supply 330. Imaging system 310 forms part of observables data capture system 116 (FIG. 1). Atomtronic station 106 can be a turnkey atomtronic system such as the QuCAL Ultracold Atom laboratory available from Cold-Quanta, Inc., Boulder Colorado.

Source 302 for atomtronics station 106 includes two modules filled with rubidium 87 ($^{87}$Rb). Other cold-molecule-type BEC-stations can include modules filled with cesium 133 ($^{133}$Cs) and/or filled with potassium 39 ($^{39}$K). $^{87}$Rb, $^{133}$Cs, and $^{39}$K are alkali elements with a single electron in their respective outer shells. Alternative source materials can include isotopes of these elements, such as $^{85}$Rb, alkaline earth metals such as strontium, other elements, and various polyatomic molecules, other bosons and fermions. In some embodiments, an atomtronics station can be configured with two or more source materials, e.g., for comparisons across source materials. Different source materials may require different laser frequencies and thus, in some cases, additional lasers.

In atomtronics station 106, $^{87}$Rb atoms can be released into a vacuum by heating one of the source modules. The heating can be effected using resistive heating generated by driving a current through a resistive element in or on the module. Alternatively, a laser can be used to heat the module and/or its contents. The vacuum into which the atoms are released is maintained by a multi-stage vacuum system 304. Vacuum system 304 can be a standard RuBECi double MOT UHV chamber, available from ColdQuanta, Inc. Released atoms travel, e.g., upwards, through one or, in other embodiments, more pre-cooling cells to a cold cell, which, in FIG. 3, is capped by an atom chip 326. In various embodiments, reservoirs of pre-cooled quantum-state carriers can be formed in one or more of these cells. Atom chip 326 has a split-wire waveguide design and an integrated optical window respectively for magnetic trapping and thru-chip optical access to trap ultracold atoms.

Vacuum system 304 can include an ion pump and getter materials to maintain the vacuum conditions within the cells. Vacuum system 304 can include opto-mechanical elements for two-dimensional and three-dimensional laser cooling, optical pumping, and optical probing for time-of-flight or in-situ imaging. In addition, vacuum system 304 can include a photo-optical imaging and projection system, e.g., with a 0.6 NA (numerical aperture) primary objective lens. There is also a two-dimensional acousto-optic beam deflector (AOD) to create dynamic two-dimensional optical potentials projected onto trapped atoms.

The (e.g., upward) movement of the atoms is primarily controlled by laser system 306. Laser system 306 includes three 780 nanometer (nm) Distributed Bragg Reflector (DBR) diode lasers respectively serving as master, cooling slave, and repump slave. In addition, there is a tapered amplifier to increase laser power for cooling. All lasers have associated current drivers, 1- or 2-stage temperature controllers, as well as laser current locking electronics for Doppler-free saturated absorption spectroscopy locking to atomic transitions and offset phase locking to the master laser. By controlling the offset frequency from the master laser, the cooling slave also achieves pump and probe functionality. Additionally, four acousto-optic modulators provide for laser frequency agility (detuning) and fast (~nanosecond) intensity modulation. In addition, there are six optical shutters for binary ON and OFF operation. A blue-detuned 760 nm semiconductor laser provides for repulsive optical potentials. The lasers are used to manipulate internal states, cool, guide, move, trap, and image the atoms. In particular, they can be used to form lattices to trap and motivate atoms as the laser beams are frequency and phase modulated in accordance with atomtronics concepts.

Atom chip 326 can be used to form a magnetic trap. In alternative embodiments, optical traps are used instead of or in addition to the magnetic trap produced by an atom chip (e.g., to trap a BEC). Thus, some embodiments dispense with an atom chip; completing the vacuum boundary with a glass or silicon wall as part of the vacuum boundary.

Laser system 306 cooperates with magnetics system 308 to define two-dimensional and three-dimensional magneto-optical traps (MOTs) and lattices. Magnetic system 308 includes permanent magnets around the pre-cooling cell and copper electromagnetic field coils including x-, y-, z-bias coils and a quadrupole transport coil around the cold cell; current through these coils generates magnetic fields that help form the MOT in the cold cell. Imaging system 310 includes two CCD cameras for characterizing the atoms in the cold cell: a Basler for time-of-flight imaging and an Andor EMCCD for in-trap imaging.

Controller 112 controls and coordinates the actions of the various other systems. Controller 112 system outputs analog and digital signals to control the various systems, e.g., to turn lasers and magnets on and off, and to control currents through atom chip 326. In an alternative embodiment, a controller includes analog inputs for monitoring and diagnostics, e.g., photo-diode signals of MOT loading. Controller 112 runs control system software on National Instruments LabVIEW to create timing files to send to electronics system 312. Controller 112 includes a National Instruments PXI chassis with a real-time environment. Analog and digital output cards connected to the PXI chassis deliver control signals to peripheral electronics. Low-noise current supplies are used for electromagnetic field coils and the atom chip. An arbitrary waveform generator is used to create and execute radio-frequency (RF) waveforms driving the two-dimensional acousto-optic deflector.

The various systems of an atomtronics station can share components. For example, atom chip 174 forms part of the electronics system, part of the magnetics system, and part of the vacuum system. Comparing FIGS. 1 and 3, recipe hardware 110 (FIG. 1) includes vacuum system 304, laser system 306, magnetics system 308, and electronics system 312 (excluding controller 112 and server interface 116). Imaging system 310 (FIG. 3) is included in observable data capture 114.

From a user's viewpoint, interaction with graphical user interface 144 (FIG. 1) sends a selected recipe to an atomtronics station and the atomtronics station returns results, e.g., in the form of a wavefunction characterization (quantum-state data descriptive of the physical state(s)) of the relevant quantum molecules in the atomtronics station. The graphical user interface allows user definitions of multi-stage shaking function generation recipes controlling 24 analog and 16 digital control lines. The GUI allows graphical visualization or control signal levels (constant, linear ramp, exponential, sinusoid, and user input functions).

Herein, use cases for atomtronics station 106 are presented: basic Bose-Einstein condensate (BEC) production, atomtronics, and shaken lattice applications. In the basic BEC use case, a user is given control over one or more of the following parameters: 1) laser cooling; 2) optical pumping; 3) quadrupole magnetic trapping and transport; 4) atom chip loading; 5) evaporation (final-stage cooling); and 6) atom-chip trap decompression and imaging. Control of laser cooling can include control over a magneto-optical trap (MOT), a compressed magneto-optical trap (CMOT), and polarization gradient cooling (PGC). This control includes control over magnetic quadrupole and bias fields, laser tuning, and stage duration. Control over optical pumping can include control over magnetic bias fields and laser pulse duration. Control over atom-chip loading can include control over magnetic quadrupole and bias fields, current in atom-chip traces, and stage duration. Control over evaporation can include control over bias fields, current in atom chip traces, radio-frequency knife frequency, radio-frequency knife power, and stage duration. Control over atom-chip trap decompression and imaging can include control over bias fields, current in atom chip traces, stage duration, time of flight (time between trap release and image), and probe pulse duration.

Which parameters are presented to a user can depend on account type (e.g., real time accounts, scheduled accounts, stand-by accounts), user/role authorization (e.g., administrators, project managers, technicians), and user selections. Users interested in creating atomtronics with specific characteristics or in exploring ways of optimizing atomtronic production can be given access to all relevant parameters. Others might be given access to only one parameter, or parameters of a single stage, e.g., a BEC evaporation stage. In the latter cases, the other stages and parameters would be pre-set, e.g., pre-optimized. In still other cases, a user who wants to use an atomtronic transistor as a starting point might have access to a preset recipe for such a transistor without any access to underlying settings.

At the end of a BEC production cycle, by tuning the variables on the prior chart, the user will have control over the total number N, the temperature T, and the chemical potential $\mu$ of the atoms. Below the critical temperature, $T_c$, there can be $N_c$ condensed atoms and $N_{th}$ thermal atoms, so the user also has control over the "condensate fraction". Given a number of condensed atoms, $N_c$, the cloud will have chemical potential $\mu$, that arises due to atomic interactions, in addition to the thermal energy associated with temperature T. Chemical potential depends on the trap "tightness" characterized by the atom-chip trap frequencies, which can be controlled by current in the chip traces and by adjusting the bias field strength.

Figure 4:
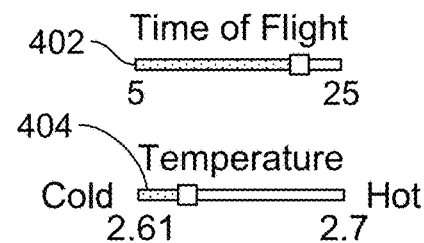
FIG. 4 is a screen shot of a graphic user interface of the atomtronics system of FIG. 1.
Figure 4:
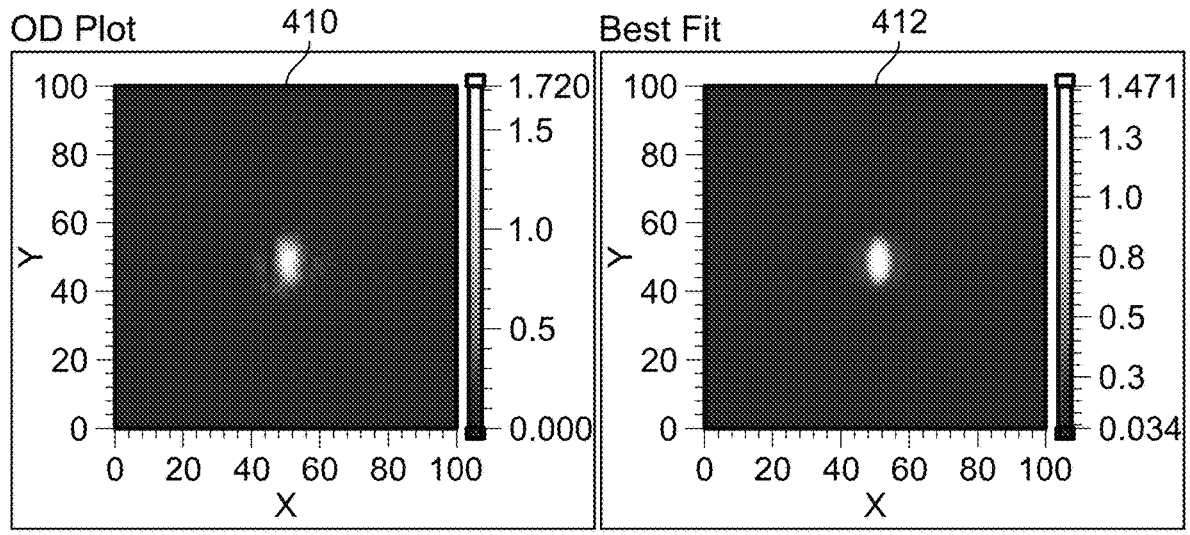
Figure 4:
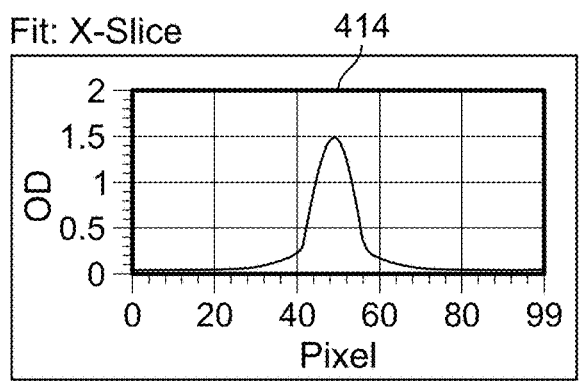
Figure 4:
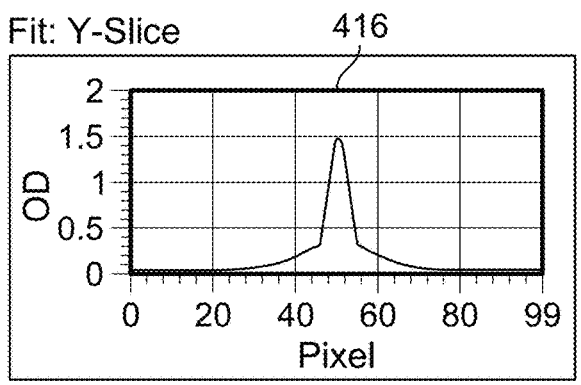

As shown in FIG. 4, graphical user interface (GUI) 144 for a computer is shown presenting, to a user, controls for time-of-flight (e.g., time after atoms are released from the trap) and for atom temperature T. A slider 402 offers a selection from 5 to 25 milliseconds (ms) for time-of-flight; the user has selected 20 ms. At ultracold temperatures, a larger time of flight is required to accurately extract thermodynamic properties of the atoms. A slider at 404 offers a selection of atomic temperature from cold to hot by tuning the RF knife frequency from 2.61 MHz to 2.70 MHz, relative to the trap bottom at 2.60 MHz; in the example of FIG. 4, the user has selected 2.63 MHz. Tuning the RF knife frequency nearer to the trap bottom produces pure BECs, while partially condensed clouds are produced for larger RF knife frequencies. Activating (clicking on) a run button 406 causes a BEC with the selected temperature to be produced by BEC-station 102.

A florescence image 410 is taken at the selected time (e.g., 20 ms after atoms are emitted from an atomtronic transistor). Fluorescence image 410 is processed to yield a best-fit image 412. Depending on the embodiment, the best-fit images and graphs might be generated by the BEC-station 106, the ATaaS server 104, or an app. Graphs 414 and 416 representing an x-dimension slice and a y-dimension slice, respectively, are also provided. In addition, a table 418 specifying numbers of atoms (numerosities) is displayed in the GUI. According to the population data represented in FIG. 4, there are 9076 total atoms, 2383 of which belong to the produced BEC, with 6693 atoms remaining thermal. From these absolute values, fractional or percentage values (e.g., BEC atoms as a percent of total atoms) can be calculated. GUI 144 can present other controls and result representatives, depending on user permissions and preferences. GUI 144 is designed to operate natively on mobile devices, as well, without loss of functionality.

Not all information that might be returned to a user qualifies as a "wavefunction characterization". For example, if an atomic clock returns a time to a user, that time does not qualify as a wavefunction characterization because it is not descriptive of a quantum state. In the case of a BEC, data specifying the number of thermal atoms left after BEC production would not qualify as a wavefunction characterizations as it does not include information descriptive of the quantum state of the BEC. However, the time or the number of thermal atoms could qualify as "based on a wavefunction characterization".

In the atomtronic use case, a user can control atomtronics station 106 to create, modify, and/or operate an atomtronic circuit or circuit element, e.g., the atomtronic transistor described in: Chapters 7-9 of "Single Atom Delivery into a Bottle Beam Trap Using an Optical Conveyor Belt and Quantum Coherent Gain in a Matterwave Transistor" (available at https://scholar.colorado.edu/concern/graduate_thesis_or_dissertations/qz20), a Ph.D. thesis by Brad Anthony Dinardo; and "Experimental Realization of Atomtronic Circuit Elements in Non-Equilibrium Ultracold Atomic Systems" (available at https://scholar.colorado.edu/concern/graduate_thesis_or_dissertations/rr171x224), a Ph.D. thesis by Seth C. Caliga.

Atomtronic circuits are defined by optical potentials that section off different portions of the atomic trap waveguide to control the flow of atoms through the "circuit." Users can have control over: arbitrary optical potentials defined by 2D AOD in a high resolution optical projection system; number of atoms, chemical potential in various parts of the circuit/device, temperature; and terminator beam on/off—which couples atoms out of the circuit to prevent unwanted interference with reflected matter waves at the circuit output. In addition to parameters specific to the atomtronics use case, the user can be provided control over the basic BEC parameters.

In the atomtronics use case, in addition to controlling the parameters for creating a BEC, the user may be provided with control over the following parameters: all-optical-BEC formation controls and/or atom-chip trap to optical lattice hand-off parameters; optical lattice light intensity to provide user control over trap depth; and shaking function, controlled by user input to a laser phase and/or frequency modulator. Regarding the lattice light intensity: at low lattice depth, atoms can tunnel between adjacent lattice sites, while at high lattice depth (high intensity) atoms are pinned to each lattice site. Regarding the shaking function: independent control over each lattice axis allows arbitrary, uncoupled shaking functions along each axis.

Figure 5:
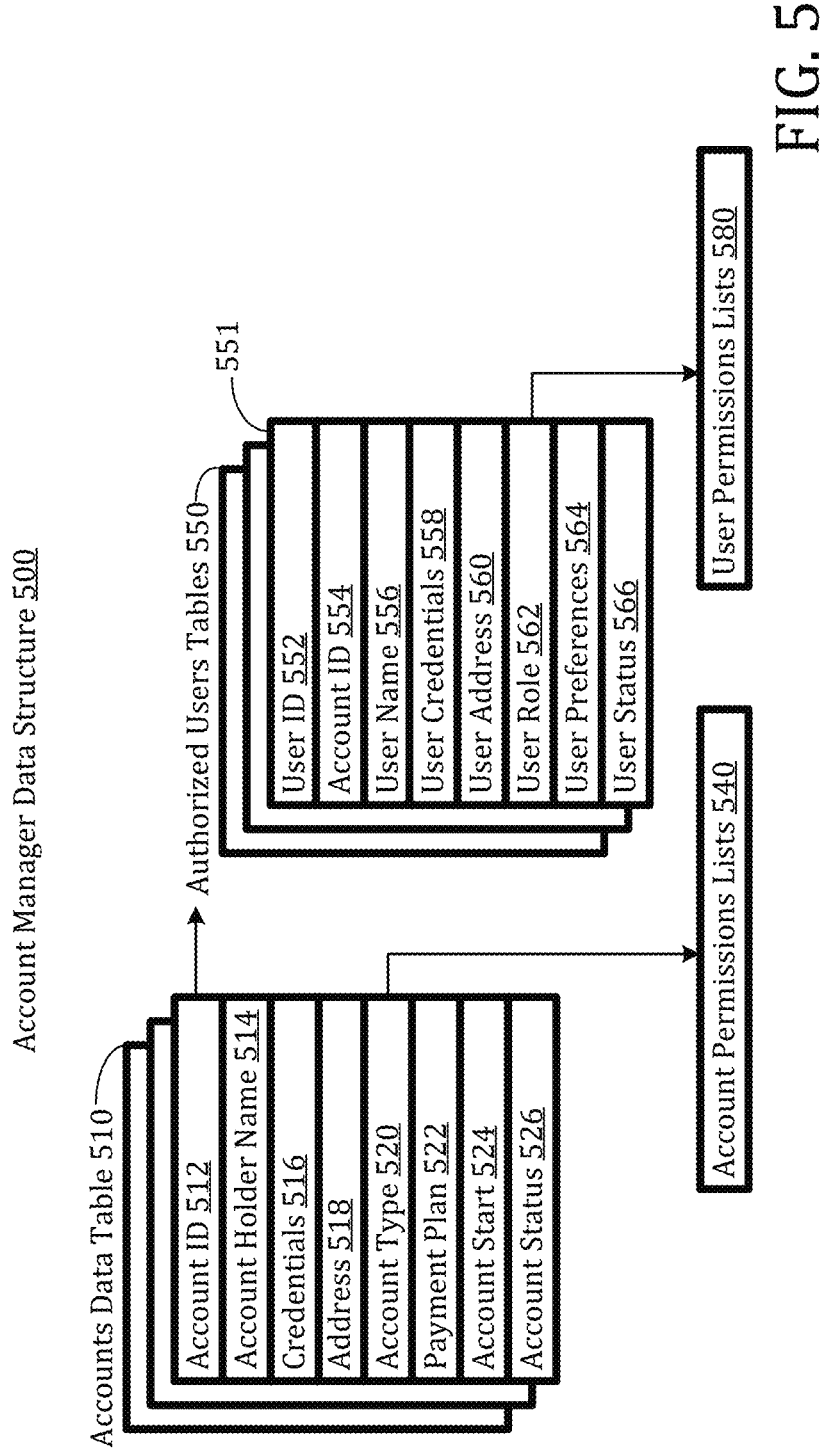
FIG. 5 is a schematic illustration of an account manager data structure for an account manager of the ATaaS system of FIG. 1.

Account manager 122 (FIG. 1) includes a data structure 500 shown in FIG. 5. Account-manager data structure 500 includes an accounts data table 510, account permissions lists 540, authorized users tables 550, and user permission lists 580. In account data table 510, the records correspond to respective accounts, while the fields correspond respectively to the following fields: account ID 512, account holder name 514, account-holder credentials 516, account-holder address 518, account type 520, payment plan 522, account start date 524, and account status 526. For each distinct account type, there is a corresponding permissions list of account permissions 540 of permissions associated with accounts of that type.

For each account ID there is a corresponding table of authorized users 550, including authorized user table 551. Each record of an authorized user table corresponds to a respective user authorized by the respective account holder to access ATaaS system 100. For each authorized user table, the records correspond to respective authorized users, while the fields include: user ID 552, account ID 554 (for reverse lookup), user name 556, user credentials 558, user IP address 560, user role 562, user preferences 564, and user status 566. For each distinct user role (administrator, project manager, senior user, trainee, etc.) there is a respective one of the user permissions lists 550 that defines user permissions (which can be a subset of the account permissions for the corresponding account type).

Figure 6:
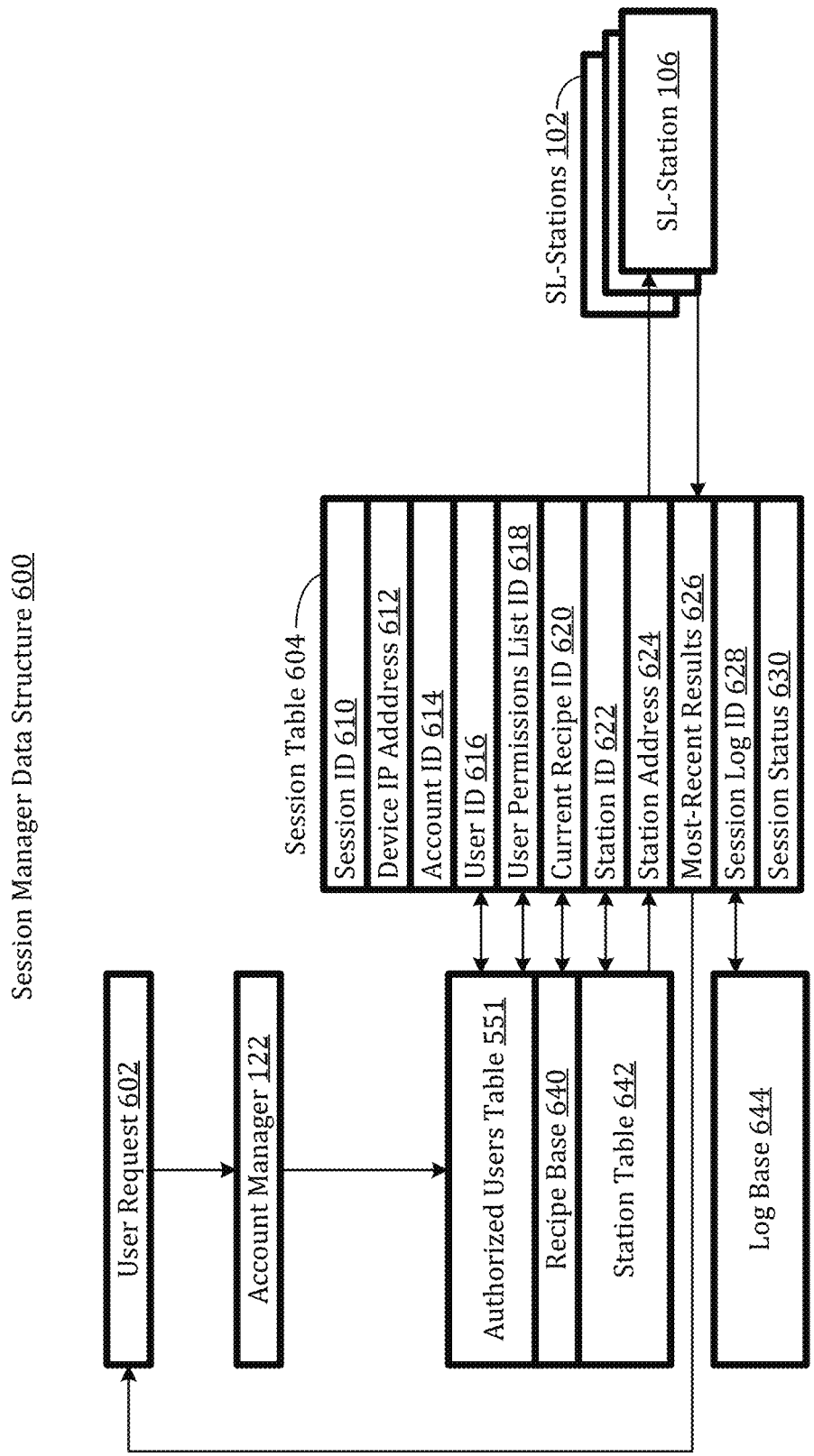
FIG. 6 is a schematic illustration of a session manager data structure for a session manager of the ATaaS system of FIG. 1.

When, at 201, FIG. 2, a user transmits a first recipe; this corresponds to transmitting a user request as indicated at 602 in FIG. 6. The account manager extracts from the request, user credentials to authenticate the user and identify the associated account. The account manager looks up the account to ensure it is active and that the user's authorization is still active. If everything checks out, the account manager forwards the request and a pointer to a user permissions list associated with the user/role.

Session manager 124 (FIG. 1) includes a session-manager data structure 600, FIG. 6, which includes a session table 604, a recipe base 640, a station table 642, and a log base 644. Each user request 602 causes session manager 124 to log records into session table 604. Each record in table 604 corresponds to a respective session. In some embodiments, there are separate session tables for each account.

The fields for session table 604 are session ID 610 (assigned by session manager 124); device IP address 612 (extracted from request) account ID 614 (provided by account manager 122 from field 554 (FIG. 5) of user table 551; user ID 616 (provided by account manager 122 from field 552 (FIG. 5) of user table 551; user permission list ID 618 (pointer to user permissions list 580 provided by account manager 122); current recipe ID 620 (extracted from original or follow-on request with entry into recipe base 640; station ID 622 (provided by session manager 124 after matching recipe to station types listed in station table 642, which identifies atomtronics stations according to type, e.g., resident quantum carriers; station address 624; most-recent results 626 (forwarded to user at device address); session log ID 628 (pointer to a log in log base 644 for the current session); and session status 630 (e.g., active, iteration number, expired). Once session manager 124 finds an available BEC-station that matches the requested recipe, it tags the recipe with the session ID and forwards the tagged recipe to the selected atomtronics station.

Figure 7A:
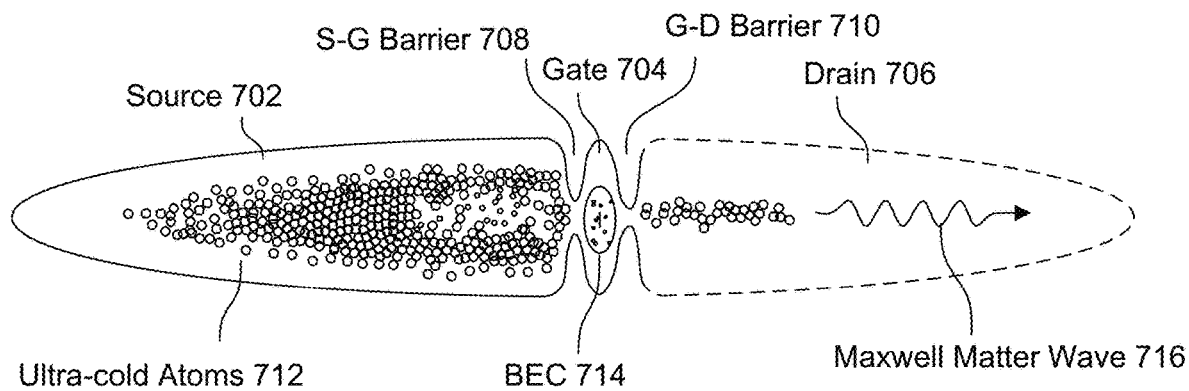
FIGS. 7A and 7B are plan and cross sectional views of an atomtronic transistor.
Figure 7B:
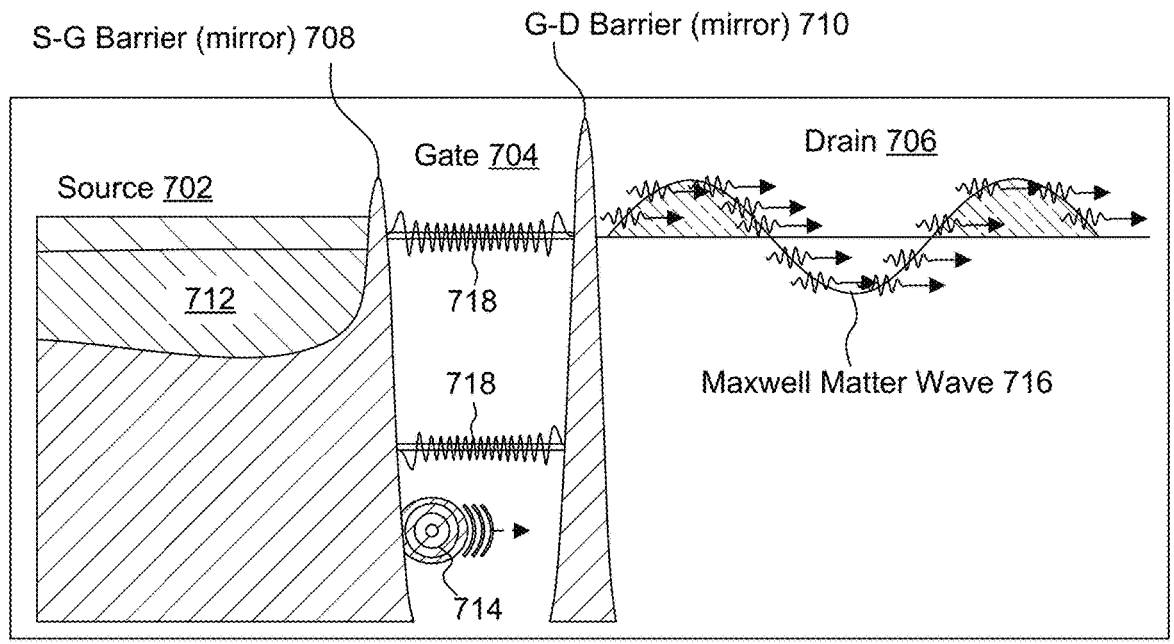

An atomtronic transistor 700, shown in FIGS. 7A and 7B, includes a source 702, a gate 704, and a drain 706. Source 702 is separated from gate 704 by a source-gate barrier 708, and gate 704 is separated from drain 706 by a gate-drain barrier 710. Such transistor structures can be formed using magnetic and light fields; for example, barriers 708 and 710 can be formed using fields of light blue-detuned with respect to light that is resonant with an energy-level transition for the ultracold atoms with which source 702 is populated. These ultracold atoms are characterized by a chemical potential $\mu_s$ that drives atomtronic transistor 700 just as a battery provides a driving electrical potential in an analogous electronic system. Ultracold atoms 712 tunnel through source-gate barrier 708, cooling to form a dipole-oscillating Bose-Einstein condensate (BEC) 714 in gate 704. The dipole-oscillating BEC oscillates back and forth between barriers 708 and 710, which in this context act as mirrors in a Fabry-Perot atom interferometer. The drain output is a Maxwell matter wave 716 with a frequency corresponding to the frequency of gate oscillation 718.

Maxwell matter waves (aka, coherent oscillatory matter waves) emerge from a perspective, complementary to de Broglie's, that matter is fundamentally a wave phenomenon whose particle aspects are revealed by quantum mechanics. Their quantum mechanical description is derived through the introduction of a matter vector potential, having frequency $\omega_0$, to Schrodinger's equation for a massive particle. Maxwell matter waves are then seen to be coherent excitations of a single-mode of the matter-wave field. In the classical regime, their mechanics is captured by a matter analog of Maxwell's equations for the electromagnetic field. As such, Maxwell matter waves enable a spectrum of systems that have useful optical analogs, such as resonant matter-wave interferometric sensors and matter-wave parametric oscillators. These waves are associated with a wavelength that is tied to the drive frequency $\omega_0$ rather than to the massive particle's energy, as is ordinarily the case with de Broglie matter waves.

Atomtronics as a service provides access to an expanded population of users by lowering the costs and expertise requirements for such access. As a result, more development toward customization and optimization of atomtronic transistors, other atomtronic devices, and networks of such devices can occur. For example, atomtronic transistors can be networked by coupling the output of one atomtronic transistor to the source and or gate of another atomtronic transistor.

Herein, "observables" refers to linear operators on the Hilbert space that constitute the possible states of the quantum system. Eigenvalues of the system are then real valued quantities such as number, phase, energy, etc. "Observables data", that is, data characterizing one or more observables, is returned by an atomtronics station. Thus, observables data can be said to characterize wavefunctions and quantum states. Results returned to a user can include observables as well as solutions to externally defined problems.

The illustrated embodiments exemplify atomtronics as a service (ATaaS) that provides cloud access for producing, manipulating, and using quantum particles in an ultra-high vacuum (below $10^{-9}$ Torr). In some embodiments, ultra-cold temperatures below 1 microKelvin and even as low as tens of nanoKelvins are achieved. Applications include cloud access to atomtronics stations for production, manipulation, and use of atomtronics, quantum sensing, quantum positioning (e.g., for navigation), quantum signal processing, quantum, information processing, quantum simulation, quantum annealing, algorithmic gate-model quantum operations, and neutral atom qubit array formation and maintenance.

Neutral atom qubits are generally encoded in environmentally insensitive electronic states of atoms. The environmental insensitivity of the qubit states makes them ideal for long-lived coherent quantum information storage but implies that the qubit-qubit interactions required for multi-qubit gate operations are not natively present. A standard approach is to make use of a third "Rydberg" state in addition to the pair of low-lying states in which the qubit is encoded to generate the required qubit-qubit interactions for multi-qubit gate operations.

Rydberg states are electronic states with highly excited principle quantum number n. The atom's electric dipole moment scales as $n^2$, which means that the interaction between a pair of Rydberg excited atoms will be strong for large n. The Rydberg-Rydberg interaction is generally dipole-dipole in nature at short distances ($<R_c$ microns), scaling as $n^4/R^3$, and van der Waals at larger distances ($>R_c$ microns), scaling as $n^{11}/R^6$, where R is the distance between the atoms and $R_c$ is a crossover distance between the two scalings that depends on species, state, and the electromagnetic environment. For a variety of parameters, $R_c$ lies in the range of a few microns, generally between 1-10 microns. Thus, the interaction can be strong for nearby atoms, but still a weak perturbation for more distant atoms.

Herein, a "quantum particle" is a particle that can assume states corresponding to eigenvalues, that is, solutions to Schrödinger's equation and superpositions thereof. Herein, the quantum particles of interest include atoms and other molecular entities. Herein, a boson is a subatomic particle the spin quantum number of which has an integer value (0,1,2 . . . ). Bosons form one of the two fundamental classes of subatomic particle, the other being fermions, which have odd half-integer spin (½, ³⁄₂ . . . ) Every observed subatomic particle is either a boson or a fermion. Neutral atoms with an even number of neutrons are bosons, while those with an odd number of neutrons are fermions. An ideal Bose gas is a quantum-mechanical phase of matter, analogous to a classical ideal gas. It is composed of bosons, which have an integer value of spin, and obey Bose-Einstein statistics. The statistical mechanics of bosons were developed by Satyendra Nath Bose for a photon gas, and extended to massive particles by Albert Einstein who realized that an ideal gas of bosons would form a condensate, namely a Bose-Einstein condensate at a low enough temperature, unlike a classical ideal gas.

Herein, "real-time" refers to actions being initiated by a station containing the cold quanta within ten seconds of a user request for those actions. "Exclusive" refers to the prevention of access to a quantum system by users other than the session owner. "Interactive" refers to actions being taken in response to user requests based on results of previous user actions in the same session.

Herein, all art labeled "prior art", if any, is admitted prior art; all art not labeled "prior art", if any, is not admitted prior art. The illustrated embodiments, variations thereupon and modifications thereto are provided for by the present invention, the scope of which is defined by the following claims.

What is claimed is:

1. A atomtronics as a service (ATaaS) process comprising:
receiving, by a cloud-based server from a first user device, a user request including a program or recipe;
sending, by the cloud-based server to an atomtronics station, a server request based on the user request;
implementation of the server request by the atomtronics station, the implementation including,
cooling quantum particles to cold temperatures in an ultra-high vacuum to provide cold quantum particles, the cold temperatures being less than one milliKelvin;
formation of an atomtronic transistor with a source populated by the cold quantum particles; and
capturing observables data characterizing a quantum-state of the cold quantum particles;

transmitting, by the atomtronics station to the cloud-based server, of a station response to the server request, the station response being based on the observables data; and transmitting, by the cloud-based server to a second user device, a server response to the user request, the server response being based on the station response, the second user device being the same as or separate from the first user device.

2. The ATaaS process of claim 1 wherein the implementation includes tunneling of the cold quantum particles to a gate of the atomtronic transistor to form a Bose-Einstein condensate in the gate.

3. The ATaaS process of claim 1 wherein the implementation includes emitting by the atomtronic transistor of a Maxwell matter wave.

4. The ATaaS process of claim 1 providing for interactive production or manipulation of the cold quantum particles during a session in which a user selects the recipe or a recipe part of a multi-part recipe based on a characterization of a quantum state of the cold quantum particles earlier in the session.

5. The ATaaS process of claim 1 wherein the user request includes the recipe that specifies procedures for producing, manipulating, or characterizing the atomtronic transistor.

6. The ATaaS process of claim 5 wherein the recipe is a branched recipe defining alternative branches to be taken depending on conditions met.

7. The ATaaS process of claim 6 wherein the branched recipe is an interactive branched recipe, wherein the conditions include a user decision.

8. The ATaaS process of claim 1 wherein the cold quantum particles are atoms.

9. The ATaaS process of claim 8 wherein the atoms are neutral alkali or alkaline earth metal atoms.

10. The ATaaS process of claim 1 further comprising authenticating, by the cloud-based server, a user.

11. An atomtronics as a service (ATaaS) system comprising:
an atomtronics station including
a controlled environment for implementing recipes for altering wavefunctions of cold quantum particles having a temperature of less than one milliKelvin so as to form or use an atomtronic transistor,
a wavefunction characterization system for generating results either including characterizations of the wavefunctions or based on characterizations of the wavefunctions, and
a server interface for receiving the recipes and for transmitting the results; and
a cloud-based server including
a station interface for transmitting the recipes to and receiving the results from the atomtronics station,
a device interface for receiving from user devices requests specifying recipes and for transmitting respective results to the user devices, and
a session manager for managing interactions between authenticated users and the atomtronics station, the session manager being coupled to the station interface and the device interface.

12. The ATaaS system of claim 11 wherein the implementing includes ultracold atoms tunneling from a source of the atomtronic transistor to a gate of the atomtronic transistor to form a Bose-Einstein condensate in the gate.

13. The ATaaS system of claim 11 wherein the implementing includes transmitting by the atomtronic transistor of a Maxwell matter wave.

14. The ATaaS system of claim 11 wherein the cloud-based server further includes an account manager for managing accounts, the managing including managing financial transactions with the accounts and authenticating users associated with the accounts.

15. The ATaaS system of claim 11 providing for interactive production or manipulation of the cold quantum particles during a session in which a user selects a recipe or recipe part of a multi-part recipe based on a characterization, received earlier in the session, of a quantum state of the cold quantum particles.

16. The ATaaS system of claim 11 wherein a request of the requests includes a recipe that specifies procedures for producing, manipulating, or characterizing the cold quantum particles.

17. The ATaaS system of claim 16 wherein the recipe is a branched recipe defining alternative branches to be taken depending on conditions met.

18. The ATaaS system of claim 17 wherein the branched recipe is an interactive branched recipe, wherein the conditions include a user decision.

19. The ATaaS system of claim 11 wherein the cold quantum particles are atoms.

20. The ATaaS system of claim 19 wherein the atoms include neutral alkali or alkaline earth metal atoms.

* * * * *